(12) United States Patent
Ando et al.

(10) Patent No.: US 6,605,035 B2
(45) Date of Patent: Aug. 12, 2003

(54) ENDOSCOPE

(75) Inventors: Tadashi Ando, Saitama (JP); Tadasu Kobayashi, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/945,805

(22) Filed: Sep. 5, 2001

(65) Prior Publication Data

US 2002/0028983 A1 Mar. 7, 2002

(30) Foreign Application Priority Data

Sep. 7, 2000 (JP) .......................... 2000-270953
Mar. 30, 2001 (JP) .......................... 2001-102152

(51) Int. Cl.$^7$ ................................ A61B 1/04
(52) U.S. Cl. .................... 600/127; 600/129; 600/175
(58) Field of Search ................. 600/127, 129, 600/175

(56) References Cited

U.S. PATENT DOCUMENTS

| 4,794,911 A | * | 1/1989 | Okada ......................... 600/127 |
| 4,919,114 A | * | 4/1990 | Miyazaki ..................... 600/110 |
| 5,454,366 A | * | 10/1995 | Ito et al. ....................... 600/109 |
| 5,782,751 A | * | 7/1998 | Matsuno ....................... 600/157 |
| 5,894,369 A | * | 4/1999 | Akiba et al. .................. 359/820 |

* cited by examiner

Primary Examiner—Linda C. M. Dvorak
Assistant Examiner—Jocelyn Ram
(74) Attorney, Agent, or Firm—Oliff & Berridge, PLC

(57) ABSTRACT

The insertion part of the endoscope has a cap fixed to the distal end face of a distal end body. A projecting part of the cap is inserted in a receiving hole formed on the distal end face. The inserted projecting part is fixed to the distal end body with a screw inserted in an attachment hole, which is formed on the periphery of the distal end body and connects with the receiving hole. Bending rubber covers the attachment hole as well as the outer periphery of the distal end body.

10 Claims, 12 Drawing Sheets

F I G. 5
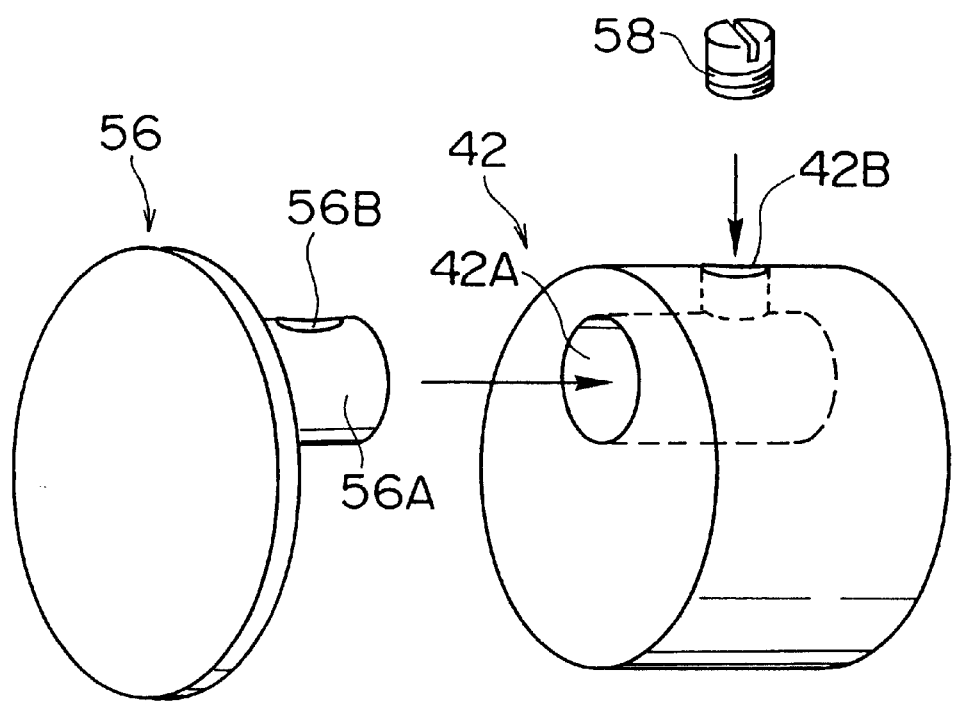

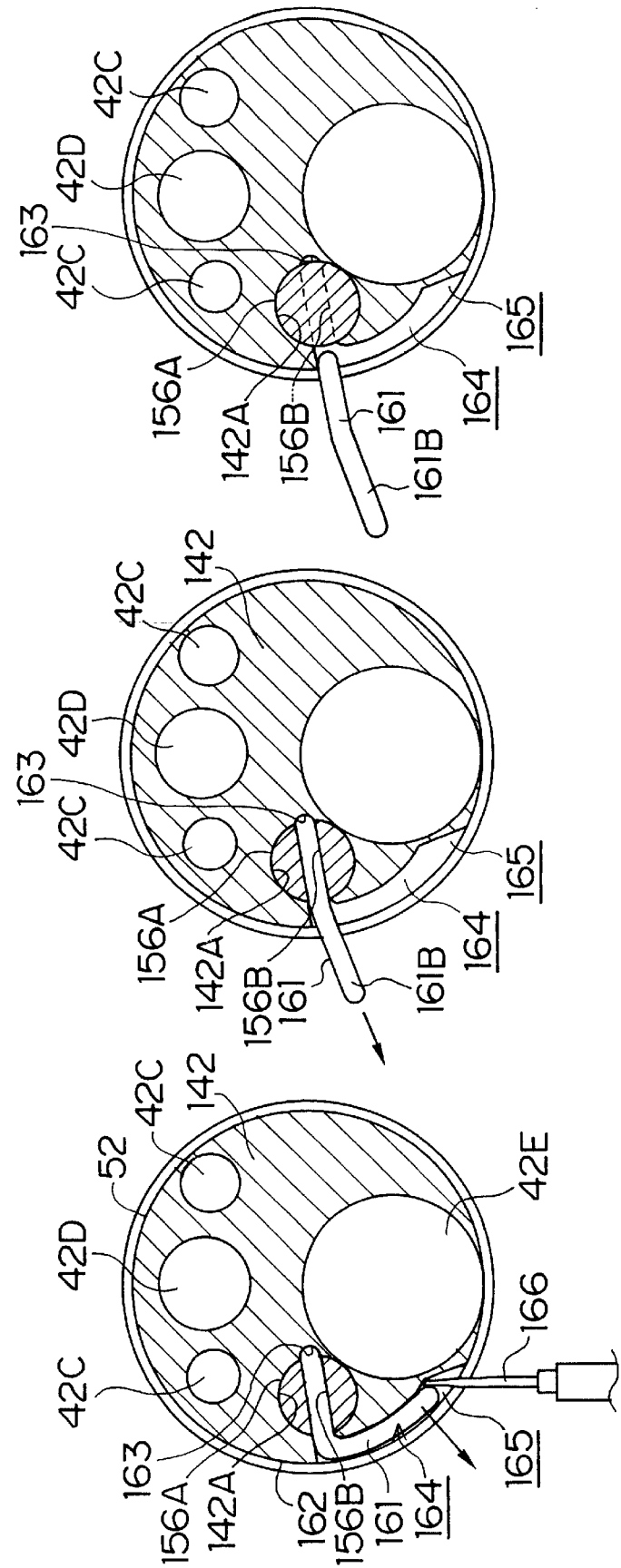

F I G. 1 2 (a)
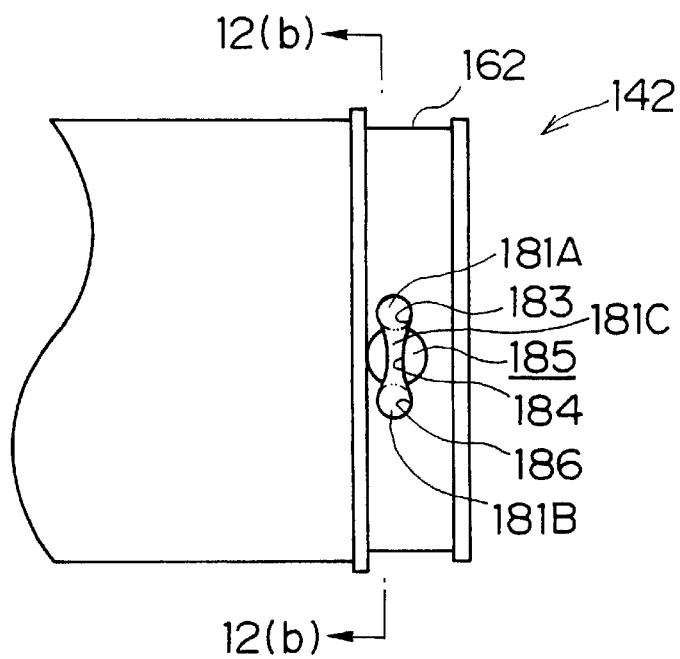
F I G. 1 2 (b)
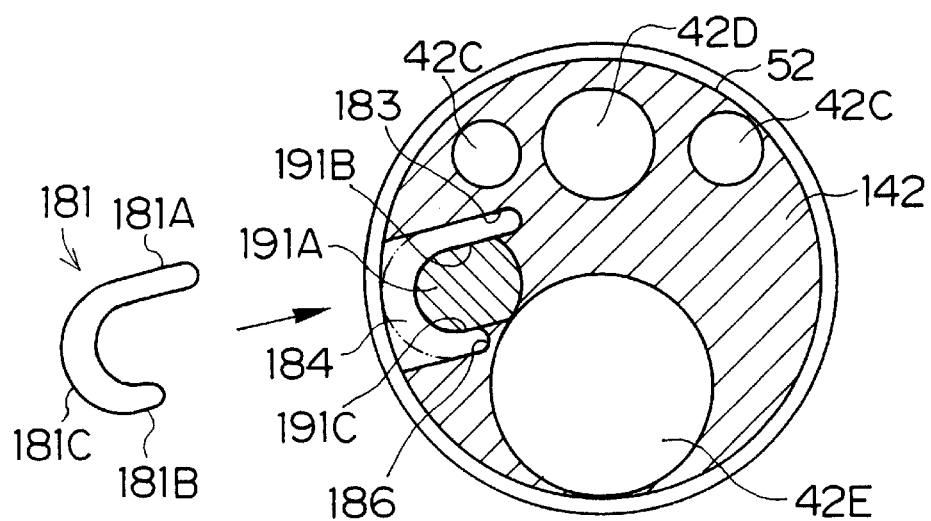

ENDOSCOPE

BACKGROUND OF THE INVENTION

1. Field of the Invention

The present invention relates to an endoscope which is specifically used for observing the trachea and the bronchi.

2. Description of the Related Art

An insertion part of the endoscope to be inserted in a subject has a base end, which is connected with a hand control part. The insertion part is constructed in the following order: a flexible part, a bending part, and a distal end assembly, when viewed from the base end to the distal end. The flexible part has an almost the whole length in the insertion part, and its outer periphery is covered with an external cover, which is made of polyurethane or similar material. The bending part has a joint-ring assembly, in which a number of joint rings are continuously connected with each other through connecting pins. A distal end sleeve, which positions at the most distal end of the joint-ring assembly, is coupled and fixed to a metal distal end body constituting the distal end assembly. The outer periphery of the joint-ring assembly is covered with a covering member, which is constructed of a metal net and an elastic body such as EPDM and is referred to as a bending rubber. The bending rubber is arranged to cover the distal end assembly also. Then, a resin cap is attached on the distal end face of the distal end assembly.

FIG. 13 shows a conventional cap 1. The cap 1 is fixed by screwing a metal screw 5 through a threaded attachment hole 2 into a threaded hole 4 formed at a distal end body 3, and the attachment hole 2 is then filled up with adhesive 6. This structure secures electric insulation and airtightness of the bending part and the distal end assembly.

In the conventional endoscope, however, the adhesive for filling up the attachment hole sometimes comes off and the screw may be exposed to the outside. If the screw is exposed and a surgical device using an electric current in a high frequency touches the screw, the electric current flows into interior devices provided in the insertion part, and the interior devices may be damaged. Another problem in the exposure of the screw is that an electric current may flow into the body of the subject through the screw because the distal end assembly without the adhesive does not have proper electric insulation.

Moreover, if the adhesive comes off while the insertion part is in the body of the subject, the adhesive may be left in the body as a foreign object; hence, improvement of the endoscope has been desired, specifically for an endoscope that is used for observing the trachea and the bronchi.

SUMMARY OF THE INVENTION

The present invention has been developed in view of the above-described circumstances, and has as its object the provision of an endoscope, with which a distal end cap can be fixed while securing an absolute insulation and also which does not allow a foreign object to be left in the body of the subject.

In order to achieve the above-described objects, the present invention is directed to an endoscope, comprising: an insertion part to be inserted in a subject, a distal end portion of the insertion part having a projecting part receiving hole on a distal end face of the insertion part, an axis of the projecting part receiving hole being in a longitudinal direction of the insertion part, the projecting part receiving hole receiving a projecting part of a cap member attached on the distal end face of the insertion part, the distal end portion having an attachment hole on an outer periphery of the distal end portion, the attachment hole connecting with the projecting part receiving hole, the attachment hole receiving a fixing member fixing the projecting part of the cap member to the distal end portion; the cap member which is attached on the distal end face of the insertion part, the cap member having the projecting part on a face of the cap member facing to the distal end face of the insertion part, the projecting part being inserted in the receiving hole of the distal end portion of the insertion part; and a covering member which covers an outer periphery of the insertion part including an opening of the attachment hole on the outer periphery of the distal end portion of the insertion part.

According to the present invention, the attachment hole for the fixing member such as a pin or a screw is formed at the outer periphery of the distal end; thus the fixing member inserted in the attachment hole is covered with the covering member and is not exposed to the outside. Therefore, the cap member can be fixed to the distal end without exposing the fixing member to the outside. Further, since the fixing member is covered with the covering member, adhesive is not required to be applied over the fixing member. Hence, no adhesive is left in the body of the subject.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 5 is a view presenting attachment of a cap in FIG. 1;

FIGS. 10(a), 10(b) and 10(c) are views presenting an operation of the fourth embodiment;

FIGS. 12(a) and 12(b) are views showing the distal end assembly in the sixth embodiment.

DETAILED DESCRIPTION OF THE PREFERRED EMBODIMENTS

Hereunder preferred embodiments will be described in detail for an endoscope of the present invention in accordance with the accompanied drawings.

Figure 1:
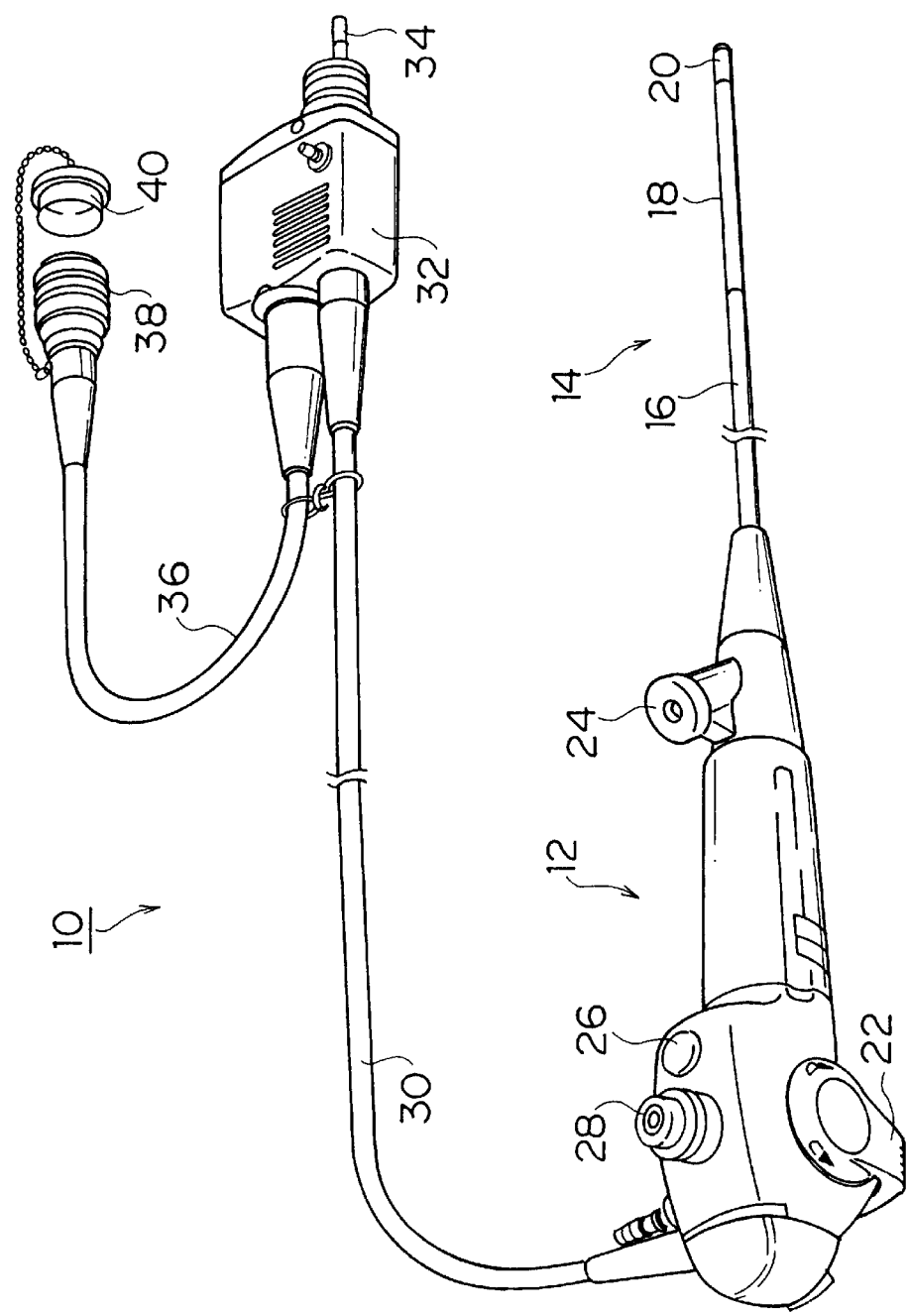
FIG. 1 is a perspective view showing a first embodiment of an endoscope of the present invention.

FIG. 1 is a perspective view of an endoscope 10, which is used for observing the trachea and the bronchi. The endoscope 10 in FIG. 1 has a hand control part 12 and an insertion part 14, of which base end is connected with the hand control part 12.

The insertion part 14 comprises a flexible part 16, a bending part 18, and a distal end assembly 20. The bending part 18 can be remotely controlled by rotating a bend control lever 22, which is provided to the hand control part 12, so that the distal end assembly 20 is pointed at desired directions.

The hand control part 12 comprises: a forceps hole 24, through which surgical instruments such as a forceps is inserted; and a shutter-release button 26; and a suction button 28 located next to shutter-release button 26. The hand control part 12 is connected with a light guide (LG) connector 32 through an LG flexible part 30. The LG connector 32 is provided with a light guide stick 34, which is connected with a light source device provided in a processor (not shown). An electric connector 38 is connected with the LG connector 32 via an elastic tube 36. A cap 40 is attached on the electric connector 38 to keep the electric connector 38 waterproof.

Figure 2:
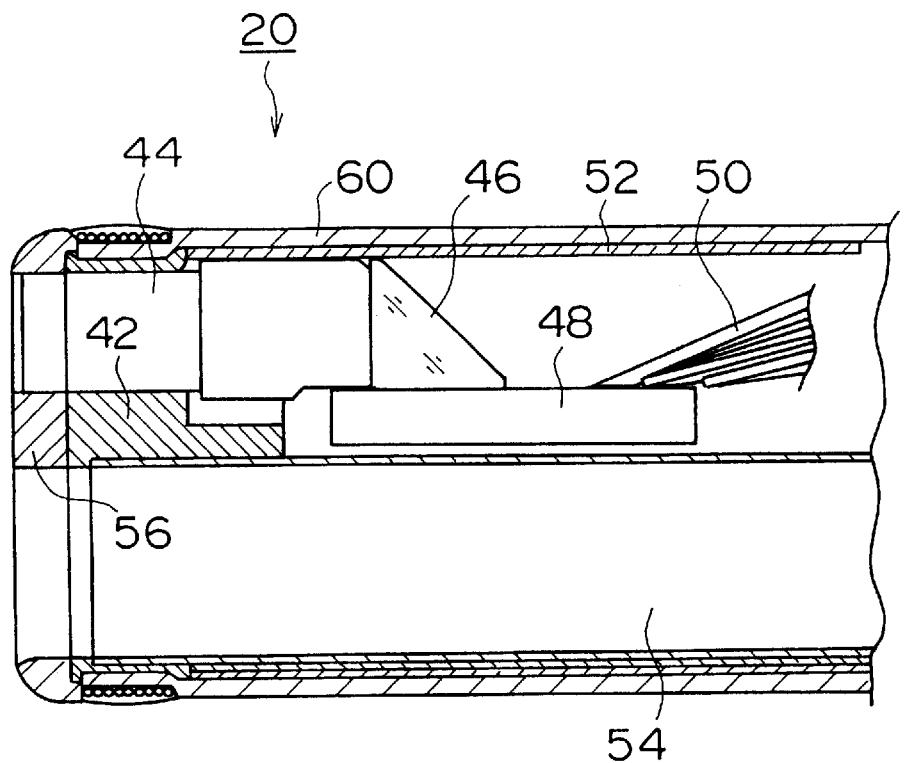
FIG. 2 is a section view showing a distal end assembly of an insertion part in FIG. 1.

FIG. 2 is a section view showing the distal end assembly 20. A lens barrel 44 for supporting a plurality of lenses (not shown) is arranged in a distal end body 42. A prism 46 is arranged at the rear of the lens barrel 44, and a solid-state imaging device (e.g., CCD) 48 is arranged on a light-exit face of the prism 46. An observed image is formed on a light-receiving face of the CCD 48 through the lenses in the lens barrel 44 and the prism 46. The image is converted into an electric signal by the CCD 48, and the converted electric signal is outputted through a signal cable 50 and the electric connector 38 in FIG. 1 to the processor (not shown). The electric signal outputted to the processor is then outputted to a monitor (not shown) after being converted into a video signal by a signal-processing unit.

A distal end sleeve 52 is positioned at the most distal end of the joint-ring assembly of the bending part 18, and the distal end of the distal end sleeve 52 is coupled and fixed to the distal end body 42. The distal end body 42 is made of metal, and has illuminating windows 42C and an observing window 42D (shown in FIG. 3). A surgical instrument channel pipe 54 is inserted in the distal end body 42. The surgical instrument channel pipe 54 is connected to a surgical instrument guiding part 42E (shown in FIG. 3), and is also connected to the forceps hole 24 in FIG. 1 through a forceps tube (not shown).

Figure 3:
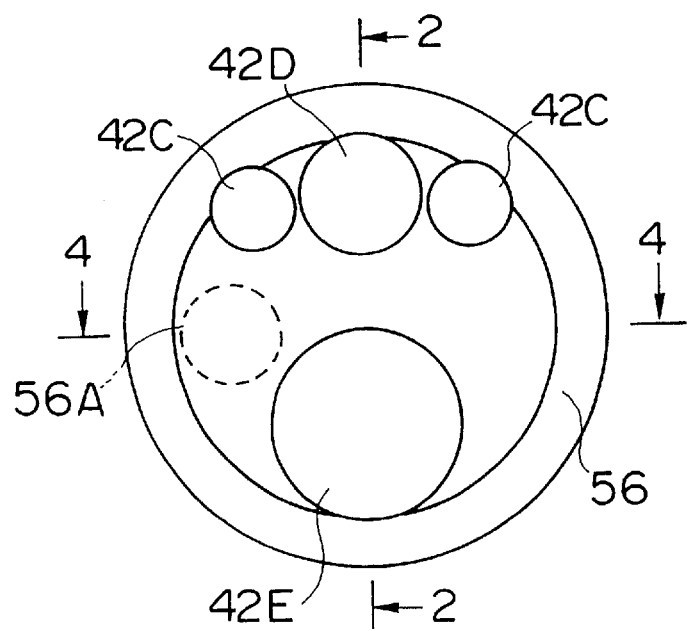
FIG. 3 is a front view showing a distal end face of the distal end assembly in FIG. 1.
Figure 4:
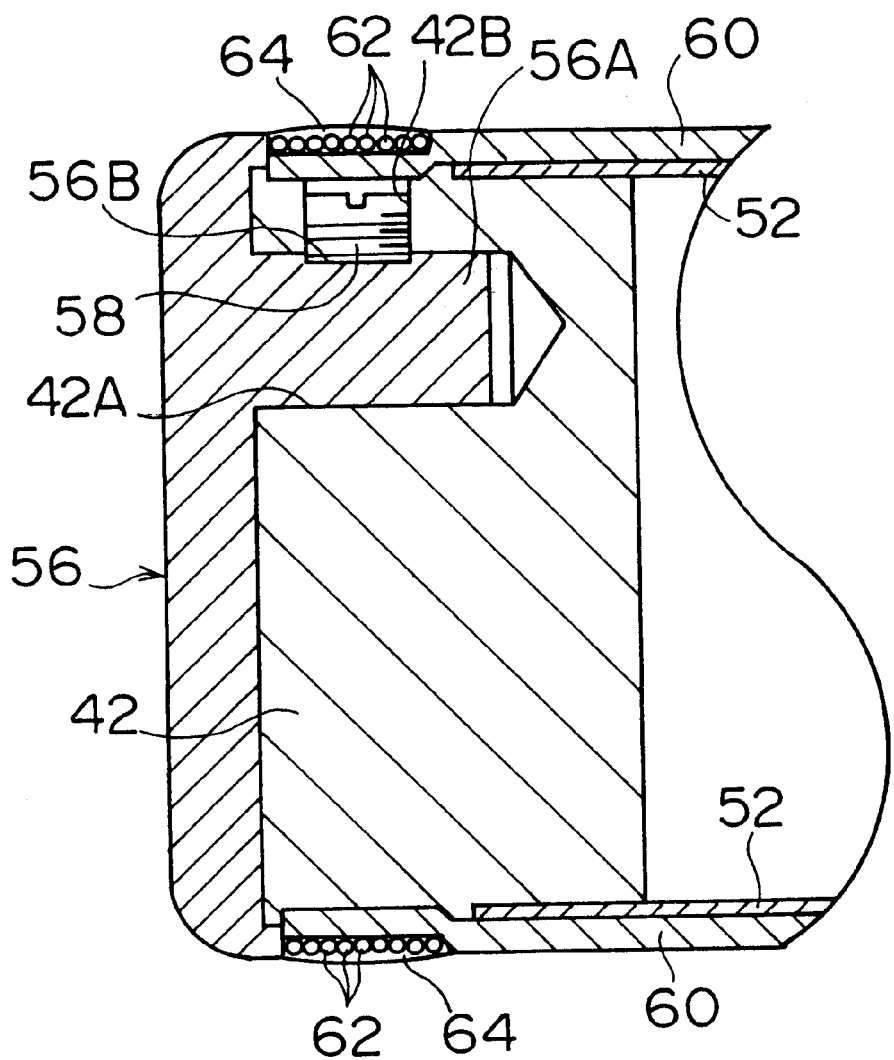
FIG. 4 is a section view showing the distal end assembly along a line 4—4 in FIG. 3.

As shown in FIGS. 2 and 3, a cap 56 is attached on the distal end face of the distal end body 42 of the distal end assembly 20, in order to cover the distal end body 42 and prevent it from being exposed to the outside. The cap 56 is made of plastic such as polysulfone. The cap 56 has openings facing the illuminating windows 42C, the observing window 42D and the surgical instrument guiding part 42E. As shown in FIG. 4, a substantially cylindrical projecting part 56A is provided on a connecting face of the cap 56, and the projecting part 56A has a flat part 56B.

A receiving hole 42A, in which the projecting part 56A is inserted, is formed on the distal end face of the distal end body 42. A threaded attachment hole 42B connecting with the receiving hole 42A is formed from the outer periphery of the distal end body 42. The flat part 56B is arranged so as to face a mouth of the attachment hole 42B opening in the receiving hole 42A. The projecting part 56A is inserted in the receiving hole 42A, and a metal screw (setting pin) 58 is screwed in the attachment hole 42B so that the tip of the screw 58 pushes the flat part 56B, whereby the cap 56 is fixed to the distal end body 42.

A covering member or bending rubber 60 covers the distal end body 42 and the outer periphery of the bending part 18. The bending rubber 60 is made of EPDM for example. The distal end of the bending rubber 60 is tightly bound on the distal end body 42 with a string 62 while contacting with the rim face of the cap 56. The string 62 is coated with adhesive 64 so as to firmly fix the bending rubber 60 to the distal end body 42. The bending rubber 60 covers the entire outer periphery of the bending part 18 in FIG. 1.

Now an operation of the endoscope 10 which is constructed as described above will be described.

The bending part 18 of the endoscope 10 is covered with the bending rubber 60, and the cap 56 is attached on the distal end face of the bending part 18. As shown in FIG. 5, in order to cover the bending part 18, the projecting part 56A of the cap 56 is first inserted in the receiving hole 42A of the distal end body 42. Then, the screw 58 is screwed in the attachment hole 42B so that the tip of the screw 58 pushes the flat part 56B. The cap 56 is thereby fixed to the distal end body 42.

Next, as shown in FIG. 4, the distal end body 42 and the outer periphery of the bending part 18 are covered with the bending rubber 60. Therefore, the bending rubber 60 covers the attachment hole 42B, and the screw 58 is thus covered completely with the bending rubber 60.

After that, the string 62 is wound onto the distal end of the bending rubber 60, the adhesive 64 is then applied thereon, and the bending rubber 60 is thus fixed securely to the distal end body 42.

In the endoscope 10 described above, the metal screw 58 for fixing the cap 56 is covered with the bending rubber 60; therefore, the screw 58 is not exposed to the outside and can be securely insulated.

Moreover, in the endoscope 10, since the attachment hole 42B is covered with the bending rubber 60, the screw 58 can be prevented from being loosened. Consequently, the attachment hole 42B does not have to be filled up with adhesive and the like, and hence no adhesive comes off or remains in the body of the subject. Therefore, the endoscope 10 according to the present invention is suitable for observing the trachea and the bronchi.

Figure 6:
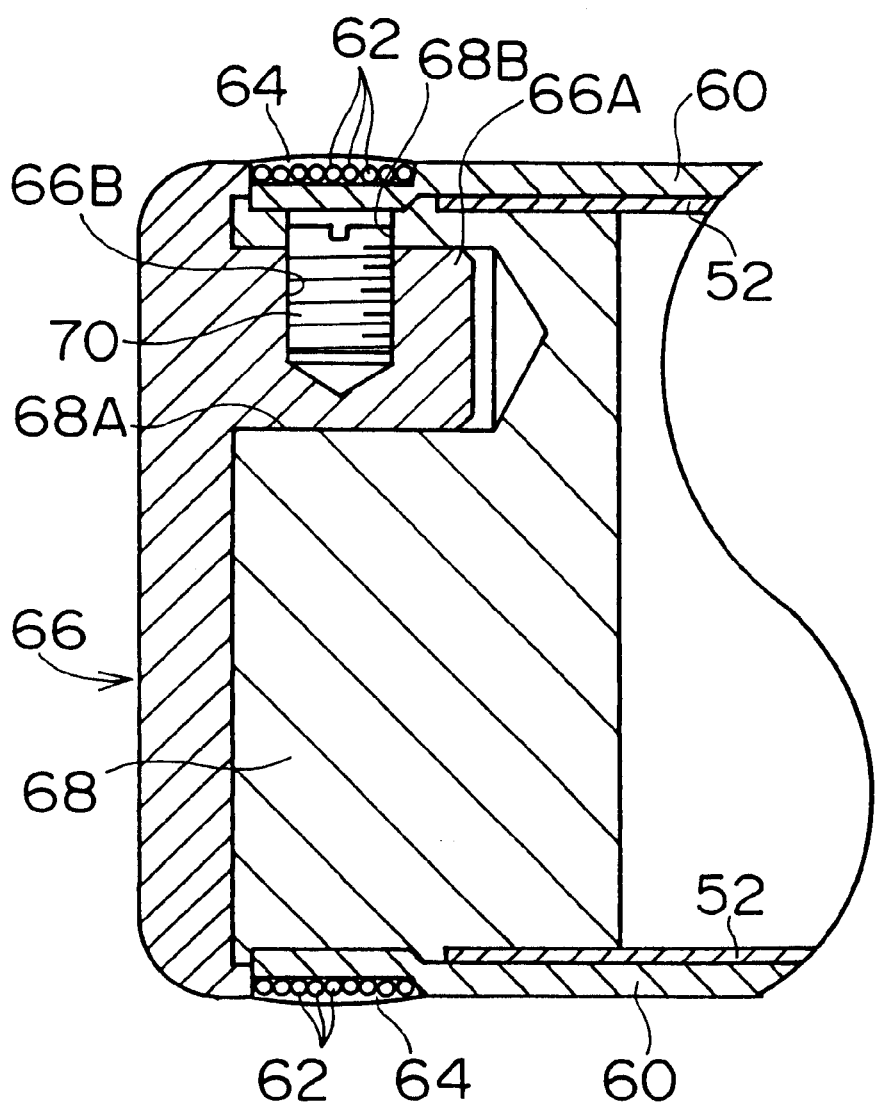
FIG. 6 is a section view showing the distal end assembly in the second embodiment.

FIG. 6 is a section view showing a distal end assembly of an endoscope according to the second embodiment of the present invention.

As seen from FIG. 6, a projecting part 66A is formed on a cap 66, and a threaded attachment hole 66B is formed at the projecting part 66 in a direction perpendicular to the axis of the projecting part 66A.

A receiving hole 68A, in which the projecting part 66A is inserted, is formed on a distal end face of a distal end body 68. An attachment hole 68B connecting with the receiving hole 68A is formed from the outer periphery of the distal end body 68. The attachment hole 68B and the attachment hole 66B of the cap 66 are arranged so as to connect with each other when the projecting part 66A is inserted in the receiving hole 68A. A metal screw 70 is screwed into the attachment hole 68B and the attachment hole 66B, and the cap 66 is fixed to the disial end body 68.

The outer peripheries of the distal end body 68 and the bending part 18 are covered with the bending rubber 60, the string 62 is wound around the distal end of the bending rubber 60, and the string 62 is then coated with the adhesive 64. The entire surface of the bending part 18 is thereby covered with the cap 66 and the bending rubber 60. Because the attachment hole 68B is covered with the bending rubber 60, the surface of the bending part 18 can be securely insulated from the outside, and at the same time the screw 70 can be prevented from being loosened. Consequently, adhesive for fixing the screw 70 is not required and no adhesive comes off and is left as a foreign object in the body of the subject.

Figure 7:
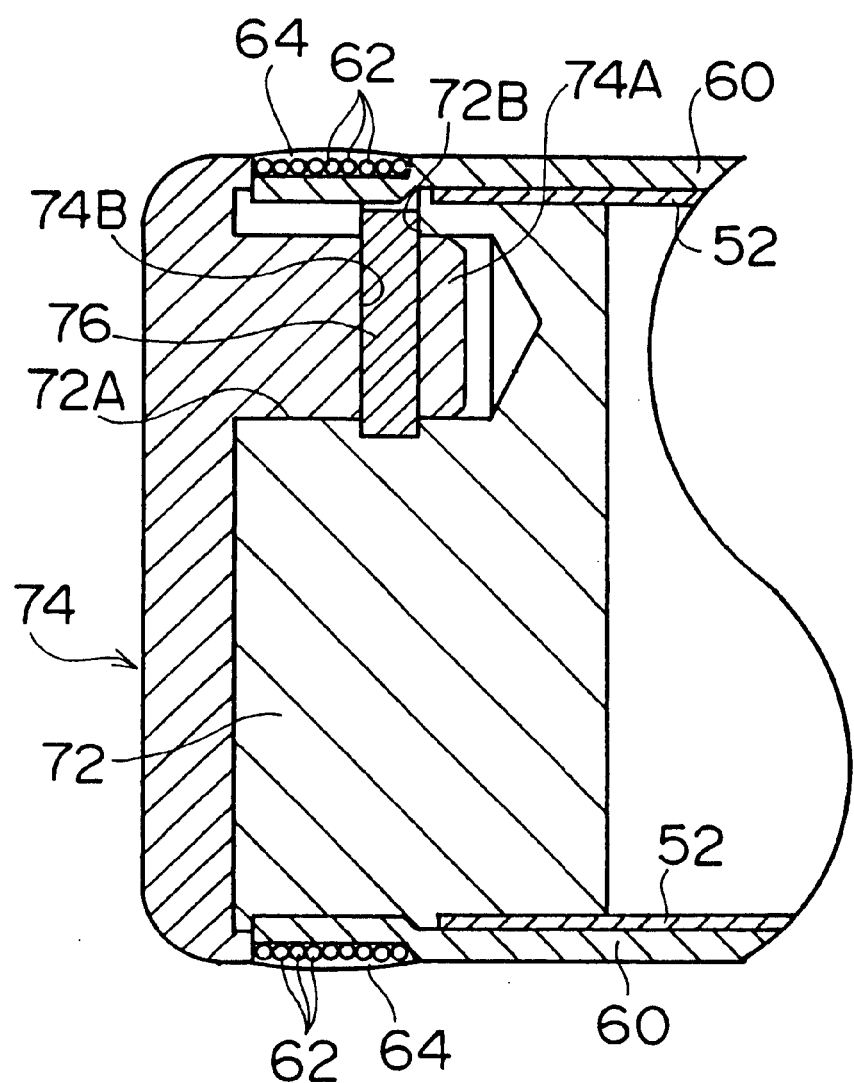
FIG. 7 is a section view showing the distal end assembly in the third embodiment.

FIG. 7 is a section view showing a distal end assembly of an endoscope according to the third embodiment of the present invention.

As seen from FIG. 7, a projecting part 74A is provided on a cap 74, and a receiving hole 74B is formed at the projecting part 74A in a direction perpendicular to the axis of the projecting part 74A. A receiving hole 72A, in which the projecting part 74A is inserted, is formed at a distal end body 72, and an attachment hole 72B connecting with the receiving hole 72A is formed from the outer periphery of the distal end body 72. The attachment hole 72B is formed so as to pass through the receiving hole 72A.

In order to attach the cap 74 on the distal end body 72, the projecting part 74A is first inserted in the receiving hole 72A, and a metal pin 76 is inserted into the receiving hole 74B through the attachment hole 72B, so that the pin 76 is inserted through the projecting part 74A. The cap 74 is thereby fixed to the distal end body 72. Next, the outer peripheries of the distal end body 72 and the bending part 18 are covered with the bending rubber 60, the string 62 is then wound around the distal end of the bending rubber 60, and the string 62 is coated with the adhesive 64. The entire surface of the bending part 18 and the distal end body 72 are thereby covered with the cap 74 and the bending rubber 60. Since the attachment hole 72B is covered with the bending rubber 60, it can be securely insulated from the outside, and at the same time the pin 76 can be prevented from being loosened. Consequently, the adhesive for fixing the pin 76 is not required, and no adhesive comes off and is left as the foreign object in the body of the subject.

Forms of the caps 56, 66 and 74 are not limited to the ones mentioned above; for example, the observing window 42D may include air and water supply nozzles for jetting air and water. Shapes of the projecting parts 66A and 76A are not limited to those mentioned above; any shapes are allowable as far as the attachment hole 66B and the receiving hole 74B are formed on the projecting parts.

Moreover, the screw 70 may be used also as a fixing means of the forceps tube 66 by inserting the tip of the screw 70 through the projecting part 66A so as to contact the tip of the screw 70 with the forceps tube 66.

Further, the present invention is not limited to the endoscope that is used for observing the trachea and the bronchi; it can be applied to any endoscope which is used for observing other objects.

Figure 8:
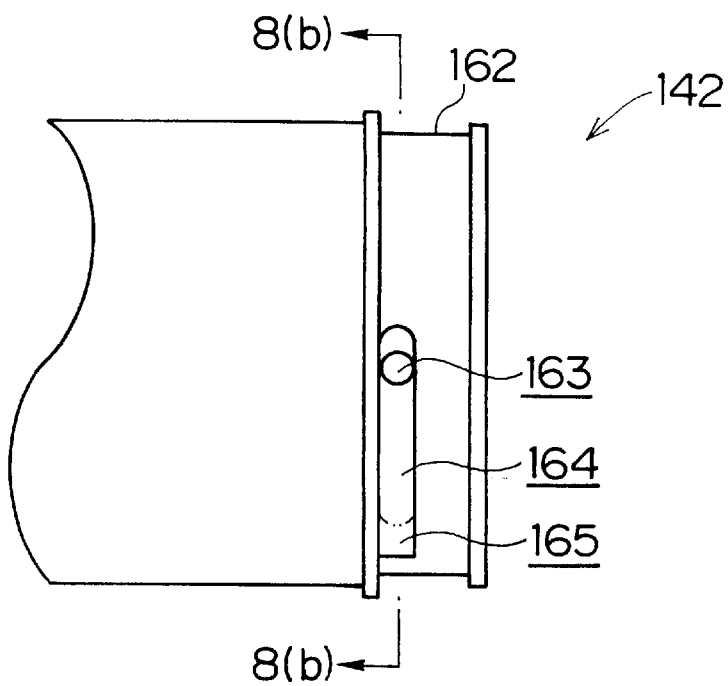
FIGS. 8(a) and 8(b) are views showing the distal end assembly in the fourth embodiment.
Figure 8:
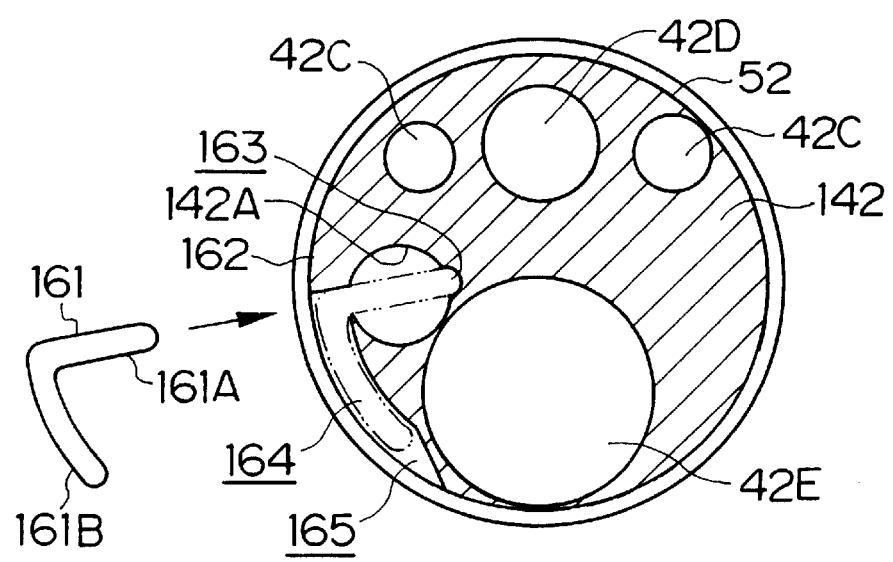

FIG. 8(a) is a side view showing a distal end assembly of an endoscope according to the fourth embodiment of the present invention, and FIG. 8(b) is a section view along a line 8(b)—8(b) in FIG. 8(a).

A cap 156 (shown in FIG. 9) is attached on a distal end face of a distal end body 142. As seen from FIG. 9, a substantially cylindrical projecting part 156A is provided on an attaching face of the cap 156, and a cap engagement hole 156B is formed as a cap engagement part at the projecting part 156A. An engagement pin 161 is inserted in the cap engagement hole 156B so as to engage the cap 156 with the distal end body 142. The engagement pin 161 is made of stainless steel, for example, and has a thickness to allow the engagement pin 161 to be easily bent with tweezers.

A receiving hole 142A, in which the projecting part 156A is inserted, is formed on the distal end face of the distal end body 142. A distal end engagement hole 163 is formed in the distal end body 142 from the outer periphery of the insertion part 14 without the bending rubber 60, from the outer periphery 162 of the distal end body 142, for example. The distal end engagement hole 163 passes through the receiving hole 142A, and serves as an engagement pin receiving hole for receiving a first portion 161A that includes a first end of the engagement pin 161. When the projecting part 156A of the cap 156 is inserted in the receiving hole 142A of the distal end body 142, the distal end engagement hole 163 connects with the cap engagement hole 156B.

As seen from FIGS. 8(a) and 8(b), a receiving groove 164 for receiving a second portion 161B including a second end of the engagement pin 161 is formed along the outer periphery of the insertion part 14 without the bending rubber 60, along the outer periphery 162 it of the distal end body 142, for example. The receiving groove 164 has a detachment groove 165 for detachment of the engagement pin 161. For providing the detachment groove 165, the receiving groove 164 is formed slightly longer than the second portion 161B of the engagement pin 161 in the direction in which the second end of the engagement pin 161 points as shown in FIG. 8(b).

In the endoscope which is constructed as described above, when attaching the cap 156 on the distal end face of the insertion part 14, specifically on the distal end face of the distal end body 142, the projecting part 156A of the cap 156 is inserted in the receiving hole 142A of the distal end body 142, whereby the distal end engagement hole 162 connects to the cap engagement hole 156B. Then, the first portion 161A of the engagement pin 161, which is bent at one part as shown in FIG. 8(b), is inserted in the distal end engagement hole 163 and the cap engagement hole 156B from the outer periphery 162 of the distal end body 142, and at the same time the second portion 161B of the engagement pin 161 is received in the receiving groove 164. Therefore, the cap 156 is securely fixed on the distal end face of the distal end body 142. In this state, the outer periphery 162 of the distal end body 142 and the outer periphery of the bending part 18 are covered with the bending rubber 60. Thus, the engagement pin 161 is prevented from being exposed to the outside while securely insulating the engagement pin 161 from the outside.

When detaching the cap 156 (e.g., in repairing the endoscope), the bending rubber 60 is removed from the insertion part 14, and a tool 166 is inserted to the detachment groove 165 in the manner shown in FIG. 10(a) so as to pull the second portion 161B of the engagement pin 161 up in a direction of an arrow in FIG. 10(a). Then, as shown in FIG. 10(b), the second portion 161B of the engagement pin 161, which protrudes from the outside of the outer periphery 162 of the distal end body 142, is picked with a tool (e.g., tweezers) (not shown), and is pulled in a direction of an arrow in FIG. 10(b). Thereby, the engagement pin 161 is easily pulled out as shown in FIG. 10(c).

As described above, the projecting part 156A of the cap 156 inserted in the receiving hole 142A of the distal end body 142 is engaged with the engagement pin 161, whereby the cap 156 can be attached so as not to fall off even though the endoscope has endured for a considerable time of use.

Moreover, the first portion 161A of the engagement pin 161 is inserted in the distal end engagement hole 163, which serves as the engagement pin receiving hole, from the outer periphery 162 of the distal end body 142 through the cap engagement hole 156B, the second portion 161B of the engagement pin 161 is received in the receiving groove 164, which is formed on the outer periphery of the distal end body 142, and the outer periphery 162 is covered with the covering member or the bending rubber 60. Thereby, the insulation and airtightness of the insertion part 14, the bending part 18 and the distal end assembly 20 are securely achieved.

Figure 13:
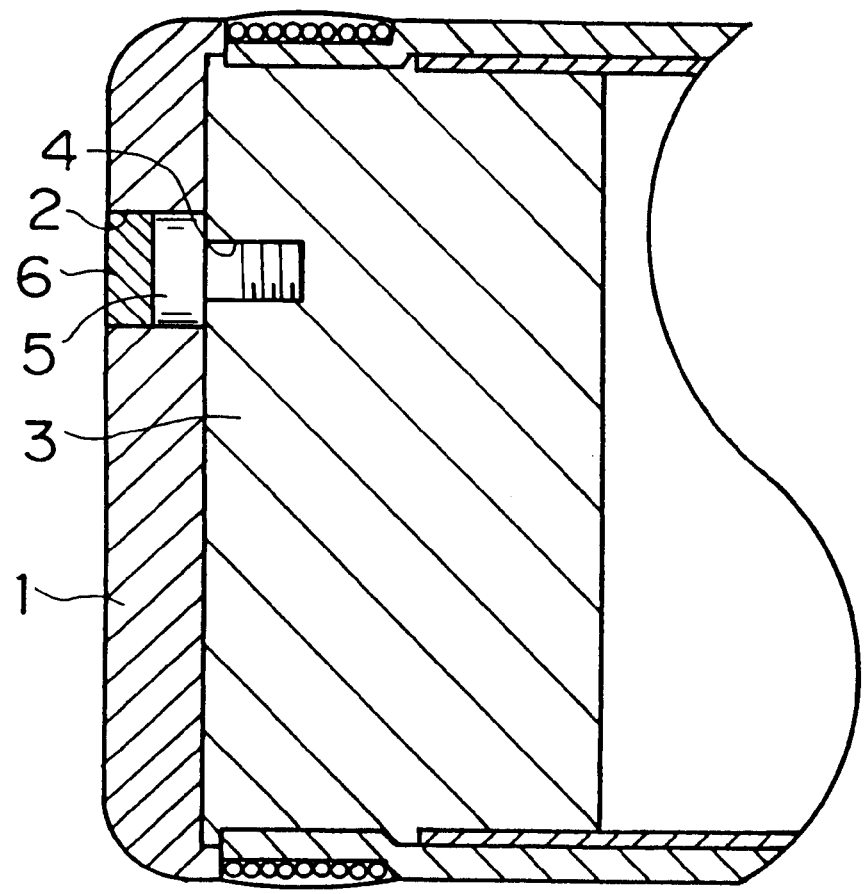
FIG. 13 is a section view showing the conventional distal end assembly.

Further, no adhesive comes off the distal end assembly according to the present invention, unlike the conventional distal end assembly in FIG. 13 that requires the adhesive 6 for filling and covering.

Furthermore, the first portion 161A of the engagement pin 161 bent at one part is inserted in the distal end engagement hole 163 from the outer periphery 162 of the distal end body 142, and the second portion 161B of the engagement pin 161 is received in the receiving groove 164; hence, the second portion 161B of the engagement pin 161 can be easily pulled up with the tool through the detachment groove 165, and can be picked with the tool (e.g., tweezers), so that the engagement pin 161 can be easily detached.

Figure 11A:
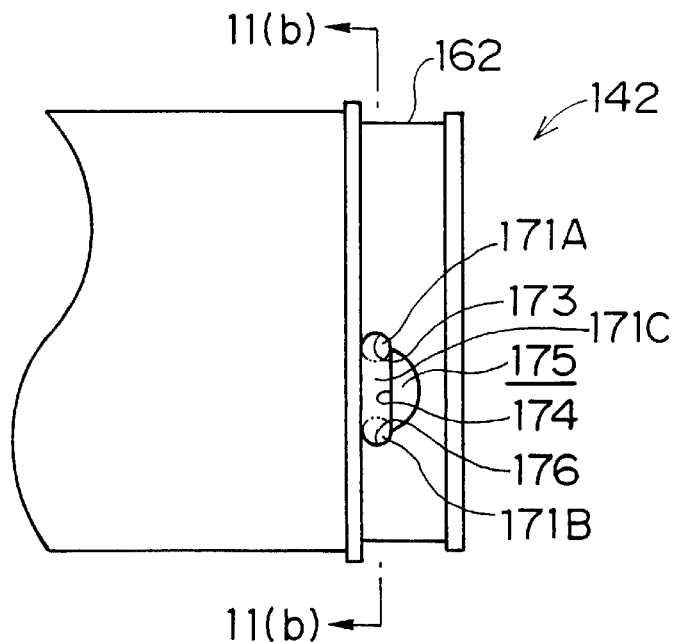
FIGS. 11(a) and 11(b) are views showing the distal end assembly in the fifth embodiment.
Figure 11B:
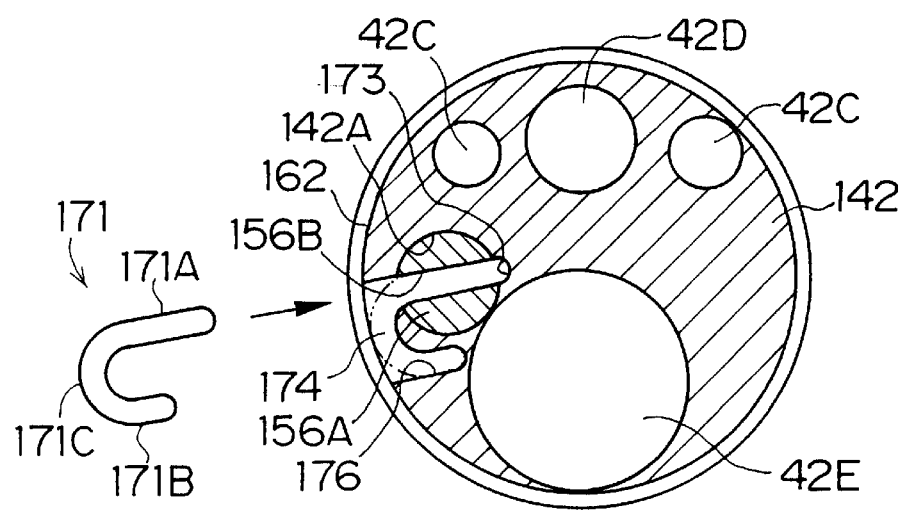

FIG. 11(a) is a side view showing a distal end assembly of an endoscope according to the fifth embodiment of the present invention, and FIG. 11(b) is a section view along a line 11(b)—11(b) in FIG. 11(a).

Figure 9:
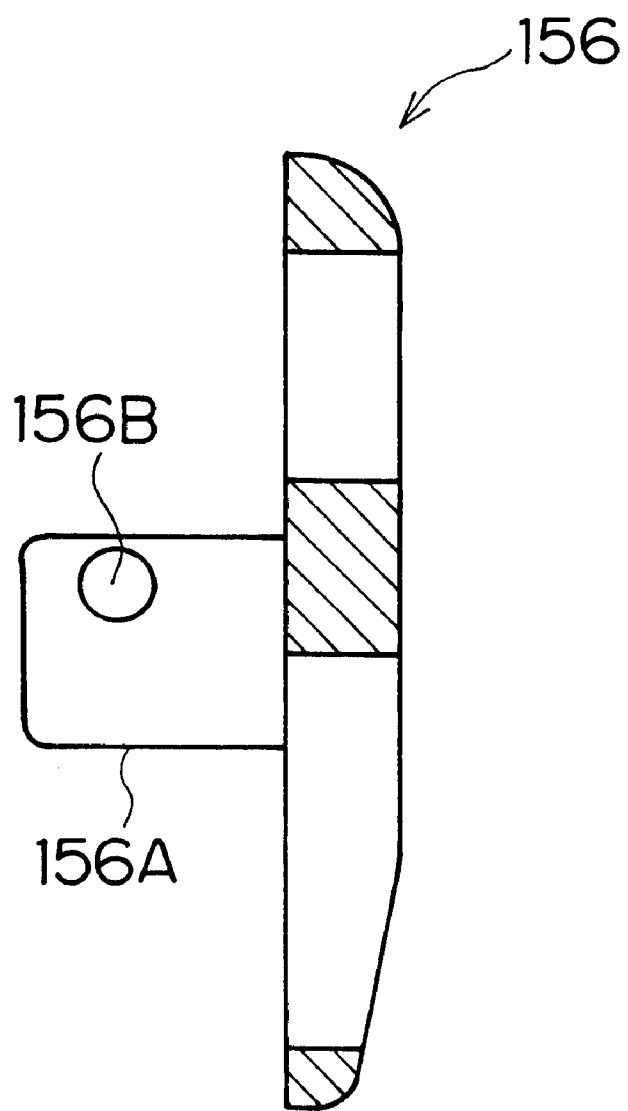
FIG. 9 is a section view showing a cap in the fourth embodiment.

The cap 156 in the fifth embodiment is the same as the one in the fourth embodiment shown in FIG. 9, and the cap engagement hole 156B is provided in the manner to go through he projecting part 156A of the cap 156. The cap 156 is engaged by inserting a first portion 171A of an engagement pin 171 of the fifth embodiment through the cap engagement hole 156B. The engagement pin 171 is bent at two parts, and the first portion 171A and a second portion 171B of the engagement pin 171 are inserted in engagement pin receiving holes 173 and 176, respectively, which are formed in the distal end body 142. A third portion 171C between the first portion 171A and the second portion 171B of the engagement pin 171 is received in a receiving groove 174, which is formed on the outer periphery 162 of the distal end face 142. In this state, the outer periphery 162 is covered with the covering member or the bending rubber 60.

The receiving groove 174 is formed so as to have its width wider toward the distal end of the distal end body 142 than a sectional diameter of the third portion 171C of the engagement pin 171, and a detachment groove 175 is thereby formed as shown in FIG. 11(a). In order to detach the engagement pin 171, a tool is inserted to the detachment groove 175 to hook the third portion 171C of the engagement pin 171 so as to pull out the engagement pin 171.

FIG. 12(a) is a side view showing a distal end assembly of an endoscope according to the sixth embodiment of the present invention, and FIG. 12(b) is a section view along a line 12(b)—12(b) in FIG. 12(a).

Instead of the cap engagement hole 156B in the fourth and fifth embodiments, engagement grooves 191B and 191C as cap engagement parts are formed on sides of a projecting part 191A of the cap 156 of the sixth embodiment. When the cap 156 is attached on the distal end body 142, the cap engagement grooves 191B and 191C connect to the engagement pin receiving holes 183 and 186 formed on the outer periphery of the distal end body 142, whereby a first portion 181A and a second portion 181B of an engagement pin 181 are insertable. The projecting part 156A of the cap 156 is held between the inserted first and second portions 181A and 181B of the engagement pin 181, and the cap 156 is engaged.

As seen from FIG. 12(a), the receiving groove 184 is formed so as to have its width wider toward both the distal end and the base end of the distal end body 142 than a sectional diameter of a third portion 181C of the engagement pin 181, and the detachment groove 185 is thus formed. In order to detach the engagement pin 181, a tool is inserted to the detachment groove 185 to pinch or hook the third portion 181C of the engagement pin 181, and the engagement pin 181 is pulled out. In that case, a thinner part can be provided to the third portion 181C of the engagement pin 181 as shown in FIG. 12(a), so that the third portion 181C of the engagement pin 181 can be pinched or hooked more easily through the detachment groove 185 with the tool and the like, hence the engagement pin 181 can be even more easily detached.

As described hereinabove, according to the endoscope of the present invention, the attachment hole of the fixing member such as the screw or the pin is formed on the outer periphery of the distal end body, which is covered with the covering member. Therefore, the cap member can be fixed to the distal end body without exposing the fixing member to the outside, and no foreign matter is left in the body of the subject.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope, comprising:

an insertion part to be inserted in a subject, a distal end portion of the insertion part having a projecting part receiving hole on a distal end face of the insertion part, an axis of the projecting part receiving hole being in a longitudinal direction of the insertion part, the projecting part receiving hole receiving a projecting part of a cap member attached on the distal end face of the insertion part, the distal end portion having an attachment hole on an outer periphery of the distal end portion, the attachment hole connecting with the projecting part receiving hole, the attachment hole receiving a fixing member fixing the projecting part of the cap member to the distal end portion;

the cap member which is attached on the distal end face of the insertion part, the cap member and projecting part being monolithic, the projecting part being on a face of the cap member facing the distal end face of the insertion part, the projecting part being inserted in the projecting part receiving hole of the distal end portion of the insertion part and fixed by the fixing member to securely fix the cap to the insertion part by way of the projecting part; and a covering member which covers an outer periphery of the insertion part including an opening of the attachment hole on the outer periphery of the distal end portion of the insertion part.

2. The endoscope as defined in claim 1, wherein an axis of the attachment hole intersects with the axis of the projecting part receiving hole at a substantially right angle.

3. The endoscope as defined in claim 1, wherein:

the projecting part of the cap member has a fixing member receiving hole; and when the projecting part is inserted in the projecting part receiving hole of the distal end portion of the insertion part, the fixing member receiving hole connects with the attachment hole of the distal end portion of the insertion part and receives the fixing member.

4. An endoscope, comprising:

an insertion part to be inserted in a subject, a distal end portion of the insertion part having a projecting part receiving hole on a distal end face of the insertion part, the projecting part receiving hole receiving a projecting part of a cap member attached on the distal end face of the insertion part, the distal end portion having an engagement pin receiving hole on an outer periphery of the distal end portion, the engagement pin receiving hole connecting with the projecting part receiving hole and receiving a first portion of an engagement pin engaging the projecting part of the cap member to the distal end portion, the distal end portion having a receiving groove on the outer periphery of the distal end portion, the receiving groove receiving a second portion other than the first portion of the engagement pin, the receiving groove including a detachment groove for detachment of the engagement pin;

the cap member which is attached on the distal end face of the insertion part, the cap member having the projecting part on a face of the cap member facing to the distal end face of the insertion part, the projecting part being inserted in the projecting part receiving hole of the distal end portion of the insertion part; and a covering member which covers an outer periphery of the insertion part including openings of the engagement pin receiving hole and the receiving groove on the outer periphery of the distal end portion of the insertion part.

5. The engagement pin which is used in the endoscope as defined in claim 4.

6. The endoscope as defined in claim 4, wherein:

the engagement pin is bent at at least one part thereof;

the engagement pin receiving hole of the insertion part receives the first portion including a first end of the engagement pin;

the receiving groove of the insertion part receives the second portion including a second end of the engagement pin; and the detachment groove of the receiving groove adjoins a position where the second end of the engagement pin is received.

7. The engagement pin which is used in the endoscope as defined in claim 6.

8. The endoscope as defined in claim 4, wherein:

the engagement pin is bent at at least two parts thereof;

the engagement pin receiving hole of the insertion part includes two holes in which the first portion including a first end and the second portion including a second end of the engagement pin are respectively inserted; and the detachment groove of the receiving groove adjoins a position where a third portion between the first portion and the second portion of the engagement pin is received.

9. The engagement pin which is used in the endoscope as defined in claim 8.

10. The engagement pin as defined in claim 9, wherein the third portion of the engagement pin has a thinner part.

\* \* \* \* \*

UNITED STATES PATENT AND TRADEMARK OFFICE
CERTIFICATE OF CORRECTION

PATENT NO. : 6,605,035 B2  Page 1 of 1
DATED : August 12, 2003
INVENTOR(S) : Tadashi Ando et al.

It is certified that error appears in the above-identified patent and that said Letters Patent is hereby corrected as shown below:

<u>Title page, Item [54] and Column 1, line 1,</u>
Change "ENDOSCOPE" to -- END CAP FIXING STRUCTURE FOR ENDOSCOPE --.

Signed and Sealed this

Thirteenth Day of January, 2004

JON W. DUDAS
*Acting Director of the United States Patent and Trademark Office*